(12) United States Patent
Babin et al.

(10) Patent No.: US 6,900,161 B2
(45) Date of Patent: May 31, 2005

(54) AZOLE OR TRIAZOLE DERIVATIVES, METHOD FOR PREPARING SAME AND USE THEREOF AS FUNGICIDES

(75) Inventors: Didier Babin, Montigny (FR); John Bernard Weston, Maisons Laffitte (FR)

(73) Assignee: Aventis Pharma S.A., Antony Cedex (FR)

( * ) Notice: Subject to any disclaimer, the term of this patent is extended or adjusted under 35 U.S.C. 154(b) by 0 days.

(21) Appl. No.: 10/754,868

(22) Filed: Jan. 9, 2004

(65) Prior Publication Data

US 2004/0162271 A1 Aug. 19, 2004

Related U.S. Application Data

(63) Continuation of application No. PCT/FR02/02435, filed on Jul. 11, 2002.

(30) Foreign Application Priority Data

Jul. 13, 2001 (FR) .............................................. 01 09331

(51) Int. Cl.⁷ ......................... A01N 43/50; C07D 233/54
(52) U.S. Cl. .................... 504/273; 504/275; 548/311.1; 548/335.5; 548/340.1; 514/396; 544/88; 544/96; 544/97
(58) Field of Search ................................ 504/273, 275; 548/311.1, 335.5, 340.1; 514/396; 544/88, 97

(56) References Cited

U.S. PATENT DOCUMENTS 2,601,275 A     6/1952   Gump et al.

FOREIGN PATENT DOCUMENTS

| EP | 0121753 | 10/1984 |
|---|---|---|
| WO | WO 00/20413 | 4/2000 |

*Primary Examiner*—Golam M M Shameem
(74) *Attorney, Agent, or Firm*—Balaram Gupta

(57) ABSTRACT

The invention concerns novel azole or triazole derivatives of formula (Ia) or (Ib), wherein: X, $Ar^1$, $Ar^2$, $Ar^3$, A, B and $R^1$ are such as defined in the description, the method for preparing same and their use as fungicides.

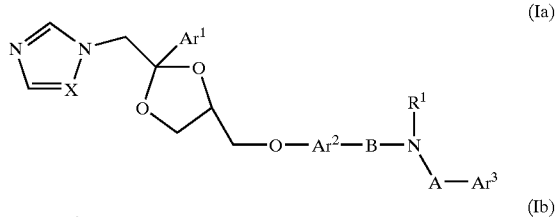

(Ia)

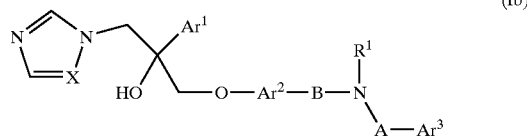

(Ib)

14 Claims, No Drawings

AZOLE OR TRIAZOLE DERIVATIVES, METHOD FOR PREPARING SAME AND USE THEREOF AS FUNGICIDES

This application is a continuation of International application No. PCT/FR02/02,435, filed Jul. 11, 2002; which claims the benefit of priority of French Patent Application No. 01/09,331, filed Jul. 13, 2001.

BACKGROUND OF THE INVENTION

1. Field of the Invention

The present invention relates to novel derivatives of azole or triazole, their preparation process and their use as fungicides.

2. Description of the Art

Numerous compounds having an antifungal activity are known in the prior art. There can be mentioned in particular the derivatives of azoles as defined in the following applications: EP 0 121 753 A (Hoechst A G), EP 0 050 298 A (Hoechst A G), U.S. Pat. No. 2,813,872 (J Schmutz), WO 00/20413 (Hoechst Marion Roussel). Moreover, the novel antifungal compounds must be able to have an improved solubility and must also be able be more easily absorbed. Nevertheless there exists a real need to implement novel antifungal compounds, the current strains being able to be or become resistant to the conventional agents in particular when the latter only possess a fungistatic activity. Finally, the incidence of *Candida albicans* as an infectious agent, is of greater and greater importance, in particular vis-à-vis immunodepressed patients, for example following infection with HIV, and therefore requires novel treatments.

A subject of the present invention is to provide novel compounds having an antifungal activity, in particular vis-à-vis the *Candida* or *Aspergillus* strains.

SUMMARY OF THE INVENTION

A subject of the invention is the compound of formula (Ia) or (Ib):

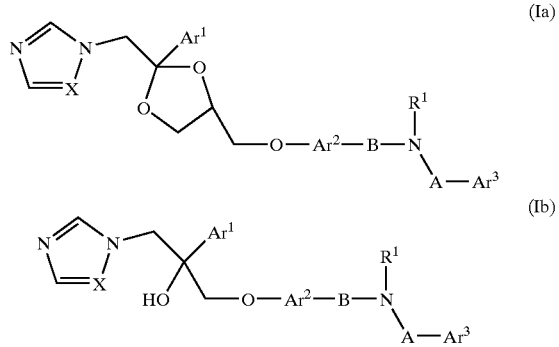

in which
X is a nitrogen atom or a CH group,
$Ar^1$ represents a carbocyclic or heterocyclic aryl non substituted or substituted by one or more $R^2$, $R^3$ or $R^4$ radicals
$Ar^2$ represents a phenylene or naphthalene non substituted or substituted by one or more $R^5$, $R^6$ or $R^7$ radicals
$Ar^3$ represents a carbocyclic or heterocyclic aryl non substituted or substituted by one or more $R^8$, $R^9$ or $R^{10}$ radicals
A represents a $(C_1-C_4)$-alkylene radical,
B represents a $-CH=CH-(C_1-C_4)$-alkylene- radical or a -cyclopropylene-$(C_1-C_4)$-alkylene- radical, the said cyclopropylene or $-CH=CH-$ radicals being non substituted or substituted by an $R^2$ and/or $R^3$ radical,
$R^1$ represents a hydrogen atom, an $-SO_3H$ group or a $(C_1-C_6)$-alkyl radical non substituted or substituted by a radical as defined for $R^2$, or an alkylene radical linked to the $Ar^3$ group
$R^2$, $R^3$, $R^4$, $R^5$, $R^6$, $R^7$, $R^8$, $R^9$ or $R^{10}$, identical or different, represent fluorine, chlorine, bromine, cyano, mono- bi- or trihalogeno$(C_1-C_8)$alkyl, mono- bi- or trihalogeno$(C_1-C_8)$-alkyloxy, hydroxy, nitro, carboxyl, formyl, $-SO_3H$, $-OSO_3H$, $(R^{11}O)_2P(O)-$, $(R^{11}O)_2P(O)-O-$, amino, $(C_1-C_8)$-alkylamino, di$((C_1-C_8)$alkyl)amino, $(C_5-C_{14})$-aryl-$(C_1-C_6)$-alkylenamino or $(C_5-C_{14})$-arylamino, $(C_1-C_8)$-alkyl, $(C_5-C_{14})$-aryl, a heterocycle optionally substituted by oxo, $(C_5-C_{14})$-aryl-$(C_1-C_6)$ alkyl, amino-$(C_1-C_6)$-alkyl, $(C_1-C_8)$-alkylamino-$(C_1-C_6)$-alkyl, di-$((C_1-C_8)$alkyl)amino-$(C_1-C_6)$-alkyl, hydroxy-$(C_1-C_6)$ alkyl, $(C_1-C_6)$-alkyloxy-$(C_1-C_6)$-alkyl, $(C_1-C_8)$-alkyloxy optionally interrupted by one or more oxygen atoms, $(C_5-C_{14})$-aryl-$(C_1-C_6)$-alkylenoxy, $(C_5-C_{14})$-aryloxy, hydroxy-$(C_1-C_6)$alkylenoxy, $(C_1-C_6)$-alkyloxy-$(C_1-C_6)$ alkylenoxy, amino-$(C_1-C_6)$-alkylenoxy, $(C_1-C_6)$-alkylamino-$(C_1-C_6)$-alkylenoxy, di$((C_1-C_8)$-alkyl)amino-$(C_1-C_6)$-alkylenoxy, methylenedioxy, $(C_1-C_6)$-alkyloxycarbonyl, $(C_1-C_6)$-alkylcarbonyl, $(C_5-C_{14})$ aryl-$(C_1-C_6)$-alkylenecarbonyl, $(C_5-C_{14})$-arylcarbonyl, $(C_1-C_6)$-alkylaminocarbonyl, $(C_1-C_6)$ alkanoylamino, $(C_1-C_6)$-alkylsulfonylamino, $(C_5-C_{14})$-arylsulfonylamino, $(C_5-C_{14})$-aryl-$(C_1-C_6)$-alkylenesulfonylamino, $(C_1-C_6)$-alkylaminosulfonyl, $(C_5-C_{14})$-aryl-$(C_1-C_6)$-alkylenaminosulfonyl, $(C_1-C_6)$-alkylsulfonyl, $(C_5-C_{14})$-aryl-$(C_1-C_8)$-alkylenesulfonyl or $(C_5-C_{14})$-aryl-sulfonyl, the said alkyl, aryl radicals or heterocycles being themselves non substituted or substituted by one or more of the groups mentioned above.
$R^{11}$ represents hydrogen, $(C_1-C_{10})$-alkyl, $(C_6-C_{14})$-aryl or $(C_6-C_{14})$-aryl-$(C_1-C_6)$-alkyl,
in all their possible stereoisomeric forms and their mixtures, as well as their physiologically acceptable addition salts and their prodrugs.

DETAILED DESCRIPTION OF THE INVENTION

All the radicals which can be found several times in the compounds of formula (I) (by (I): (Ia) or (Ib) is meant), for example, the $R^2$ radical, are independent of one another and can be identical or different.

The alkyl radicals mentioned above can be linear, branched or cyclic, saturated or mono- or poly-unsaturated. This also applies when they carry a substituent or when they are included in groups such as for example alkoxy, alkoxycarbonyl or aralkyl.

By saturated $(C_1-C_8)$-alkyl is meant the methyl, ethyl, propyl, butyl, pentyl, hexyl, heptyl, octyl, nonyl radicals, the n-isomers of these radicals, isopropyl, isobutyl, isopentyl, neopentyl, isohexyl, 3-methylepentyl, 2,3,4-trimethylhexyl, sec-butyl, tert-butyl, tert-pentyl. Among the preferred radicals there can be mentioned methyl, ethyl, n-propyl, isopropyl, n-butyl, isobutyl, and tert-butyl. By $(C_1-C_6)$-alkyl is meant the methyl, ethyl, propyl, butyl, pentyl, hexyl radicals and the n-isomers of these radicals.

By alkyloxy radical interrupted by one or more oxygen atoms, is preferably meant radicals of the O—$CH_2$—O—$(CH_2)_2$—O—$CH_3$ type.

The bivalent alkylene radicals corresponding to the monovalent radicals mentioned above are for example the methylene, ethylene, 1,3-propylene, 1,2-propylene (=1-methylethylene), 2,3-butylene (=1,2-dimethylethylene), 1,4-butylene, or 1,6-hexylene radicals.

The unsaturated alkyl radicals can contain one or more, for example one, two or three double and/or triple bonds of course, an unsaturated alkyl radical contains at least two carbon atoms. By unsaturated alkyl radical is therefore meant for example, the alkenyl radicals such as vinyl, 1-propenyl, allyl, butenyl, 3-methyl-2-butenyl or the alkynyl radicals such as ethynyl, 1-propynyl or propargyl.

By unsaturated bivalent alkylene radicals is meant the alkenylene and alkynylene radicals which can also be linear or branched. They are for example vinylene, propenylene, ethynylene or propynylene radicals.

The cycloalkyl radicals can be monocyclic, bicyclic or tricyclic. They are for example the cyclopropyl, cyclobutyl, cyclopentyl, cyclohexyl, cycloheptyl, cyclooctyl, cyclononyl, cyclodecyl, cycloundecyl, cyclododecyl, cyclotetradecyl or cyclooctadecyl radicals which if appropriate can be substituted for example by an alkyl containing 1 to 4 carbon atoms. As substituted cycloalkyl radicals, there can be mentioned 4-methylcyclohexyl, 2,3-dimethylcyclohexyl, dimethylcyclopropane and dichlorocyclopropane.

Unless otherwise specified, the alkyl or cycloalkyl radicals can be non substituted or substituted by one or more identical or different radicals chosen from $(C_1-C_6)$-alkyl, $(C_1-C_6)$-alkoxy, hydroxyl, halogen such as fluorine, chlorine and bromine, nitro, amino, trifluoromethyl, mono, —$OCF_3$, cyano, carboxyl, —$SO_3H$, —$OSO_3H$, $PO_3H_2$, $OPO_3H_2$, $(C_1-C_4)$-alkoxycarbonyl, phenyl, phenoxy, benzyl and benzyloxy. Of course this also applies when the alkyl radical forms part of a group containing it, for example such as, $(C_1-C_6)$-alkyloxycarbonyl, $(C_1-C_6)$-alkylcarbonyl or $(C_1-C_6)$-alkylaminocarbonyl.

By halogen is meant fluorine, chlorine, bromine or iodine.

By the term aryl is meant:
either the heterocyclic $(C_5-C_{14})$-aryl (=$(C_5-C_{14})$-heteroaryl) radicals, in which the carbon atoms of the ring are replaced by a heteroatom such as nitrogen, oxygen or sulfur,
or the carbocyclic $(C_6-C_{14})$-aryl radicals.

Among the carbocyclic $(C_6-C_{14})$-aryl radicals, there can be mentioned the phenyl, naphthyl, biphenylyl, anthryl or fluorenyl and quite particularly the 1-naphthyl, 2-naphthyl and phenyl radical.

Unless otherwise specified, the aryl radicals, in particular phenyl, can be non substituted or substituted by one or more identical or different radicals chosen from $(C_1-C_6)$-alkyl, $(C_1-C_6)$-alkoxy, hydroxyl, hydroxy$(C_1-C_6)$-alkyl, halogen such as fluorine, chlorine and bromine, nitro, amino, trifluoromethyl, —$OCF_3$, cyano, carboxyl, —$SO_3H$, —$OSO_3H$, $PO_3H_2$, $OPO_3H_2$, $(C_1-C_4)$-alkoxycarbonyl, phenyl, phenoxy, benzyl, benzyloxy and methylenedioxy.

In the case of monosubstituted phenyl, the substituent can be situated in position 2, 3 or 4, and preferably in position 3 or 4. Preferably, $Ar^3$ represents a phenyl substituted in position 4. In the case where the phenyl is di-substituted, the substituents can be in position 2,3 or 2,4 or 2,5 or 2,6 or 3,4 or 3,5. Preferably, when $Ar^1$ represents a disubstituted phenyl, the two substituents are in position 2,4. When this phenyl is tri-substituted the positions are the following: 2,3,4 or 2,3,5 or 2,3,6 or 2,4,5 or 2,4,6 or 3,4,5. In the same way, the naphthyl radicals or other aryl radicals can be substituted in any position, for example the 1-naphthyl radical in position 2-, 3-, 4-, 5-, 6-, 7-, and 8 and the 2-naphthyl radical in position 1-, 3-, 4-, 5-, 6-, and 7.

The $(C_5-C_{14})$-aryl group can also represent a monocyclic or polycyclic aromatic system in which 1,2,3 or 4 carbon atoms of the ring are replaced by heteroatoms, in particular identical or different from the group constituted by nitrogen, oxygen and sulfur. Among the heterocyclic $(C_5-C_{14})$-aryl (=$(C_5-C_{14})$-heteroaryl) groups there can be mentioned the 2-pyridyl, 3-pyridyl, 4-pyridyl, pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindolyl, indazolyl, phthalazinyl, quinolyl, isoquinolyl, quinoxalinyl, quinazolinyl, cinnolinyl, β-carbolinyl groups, or also of the benzo-condensed, cyclopenta-, cyclohexa-, or cyclohepta-condensed derivatives of these radicals.

The heterocyclic system can be substituted by the same substituents mentioned above for the carbocyclic system.

Of course, the above description relating the aryl groups also applies when aryl is a radical included in a group such as aryl-alkyl. As preferred examples of aryl-alkyl groups, benzyl, 1-phenylethyl or 2-phenylethyl can be mentioned.

By heterocycle, is meant preferably a radical with 5 or 6 members, non-aromatic, optionally containing one or two double bonds and one or more nitrogen or oxygen atoms substituted or non-substituted by the same substituents mentioned above for the carbocyclic system as well as the oxo radical. The invention therefore comprises the following heterocycles:

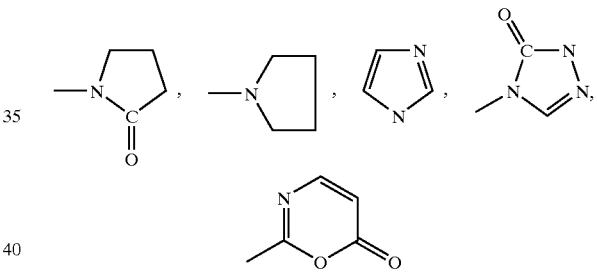

These heterocycles being able to be substituted. It can then be the following radicals:

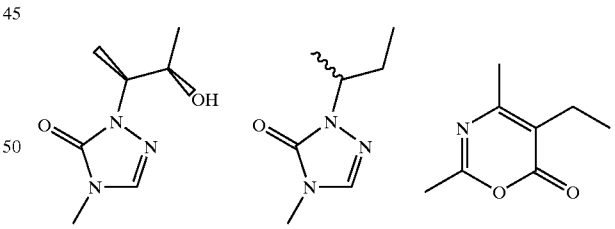

The optically active carbon atoms contained in the compounds of formula (I) can independently of each other have the R configuration or the S configuration.

The compounds of formula (I) can be in the form of pure enantiomers or pure diastereoisomers or in the form of a mixture of enantiomers, for example in the form of racemates or mixtures of diastereoisomers.

Therefore a subject of the present invention is the pure enantiomers, the mixtures of these enantiomers, the pure diastereoisomers and the mixtures of these diastereoisomers.

The invention comprises the mixtures of two or more than two stereoisomers of formula (I) and all the ratios of these stereoisomers within said mixtures.

The compounds of formula (I) can, if appropriate, be present in the form of E isomers or Z isomers. Therefore a subject of the invention is the pure E isomers, the pure Z isomers and the E/Z mixtures according to any ratio. When the compounds of formula (I) contain a cyclopropane, these compounds of formula (I) can be present in the form of cis or trans isomers. Therefore a subject of the invention is the pure cis isomers, the pure trans isomers and the cis/trans mixtures according to any ratio.

The invention also comprises all the tautomeric forms of the compounds of formula (I). The diastereoisomers, including the E/Z (or cis/trans) isomers can be separated into individual isomers, for example by chromatography. The racemates can be separated into two enantiomers by current methods such as chiral phase chromatography or by resolution methods.

The physiologically acceptable salts of the compounds of formula (I) are in particular the pharmaceutically useable or non toxic salts or salts which can be used physiologically.

When the compounds of formula (I) contain an acid group such as carboxylic acid, they are for example the salts of alkali or alkaline-earth metals such as the salts of sodium, potassium, magnesium, calcium, and also the salts formed with physiologically acceptable quaternary ammonium ions and the addition salts with acids such as ammonia and the physiologically acceptable organic amines such as for example triethylamine, ethanolamine or tris-(2-hydroxyethyl)amine.

When the compounds of formula (I) contain a basic group, they can form an addition salt with acids for example with inorganic acids such as hydrochloric, sulfuric, phosphoric acid, or with organic carboxylic acids such as acetic, trifluoroacetic, citric, benzoic, maleic, fumaric, tartaric, methanesulfonic or paratoluenesulfonic acid.

The compounds of formula (I) which contain a basic group and an acid group, such as for example guanidino and carboxylic, can be present in the form of Zwitterions (betaines), which are also included in the present invention.

When the compounds of formula (I) contain a charged ammonium group, the counter anion ($Q^-$) is preferably a monovalent anion or an equivalent of a polyvalent anion of a physiologically acceptable, non toxic, organic or inorganic, and in particular pharmaceutically acceptable, acid for example the anion or an equivalent of an anion of one of the acids mentioned above which can be used for the formation of the addition salts. $Q^-$ can be for example one of the anions (or equivalent of an anion) of a group chosen from chlorine, sulfate, phosphate, acetate, trifluoroacetate, citrate, benzoate, maleate, fumarate, tartrate, methanesulfonate and para-toluenesulfonate.

The salts of the compounds of formula (I) can be obtained by the standard methods known to a person skilled in the art, for example by combining a compound of formula (I) with an organic or inorganic acid or a base in a solvent or a dispersant or from another salt by cation or anion exchange.

The invention also includes all the salts of the compounds of formula (I) which, because of their low physiological acceptability, are not directly useable as a medicament, but are useable as intermediate products for implementing subsequent chemical modifications at the level of the compounds of formula (I) or as starting products for the preparation of physiologically acceptable salts.

The present invention also includes all the solvates of the compounds of formula (I) for examples the hydrates, the solvates formed with alcohols, and all the derivatives of the compounds of formula (I), for example the esters, prodrugs and other physiologically acceptable derivatives, as well as the metabolites of the compounds of formula (I).

A subject of the invention is also the prodrugs of the compounds of formula (I) which can be converted to compounds of formula (I) in vivo under physiological conditions. The prodrugs of the compounds of formula (I), namely the chemically modified derivatives of the compounds of formula (I) in order to obtain properties improved as desired, are known to a person skilled in the art.

For more information on the type of prodrug envisaged in the present invention, the following works can be mentioned: Fleicher et al., Advanced Drug Delivery Review 19 (1996) 115–130; Design of prodrugs, H. Bundgaard, Ed., Elsevier, 1985; H. Bundgaard, Drugs of the Future 16 (1991) 443; Saulnier et al. Bioorg. Med. Chem. Lett. 4 (1994) 1985; Safadi et al. Pharmaceutical Res. 10 (1993) 1350. Among the suitable prodrugs of the compounds of formula (I) there can be mentioned preferably:

the prodrugs in the form of esters of the carboxylic, sulfonic or phosphonic groups, when, for example, $Ar^3$ is substituted respectively by a —$CO_2H$, —$SO_3H$ or —$PO_3H$ group.

the prodrugs in the form of acyl and carbamate for the groups containing an acylable nitrogen such as the amino or guanidine groups.

the prodrugs in the form of quaternary derivatives of cyclic or non cyclic nitrogen (substituted benzyl).

In the prodrugs which are acylated or in the form of carbamate, one or more times, for example twice, a hydrogen atom situated on the nitrogen atom is replaced by an acyl or carbamate group. Among the preferred acyl or carbamate groups, there can be mentioned the $R_{12}CO—$, $R_{13}OCO—$ groups, in which $R_{12}$ is a hydrogen or a ($C_1$–$C_{18}$)-alkyl, ($C_3$–$C_{14}$)-cycloalkyl, ($C_3$–$C_{14}$)-cycloalkyl-($C_1$–$C_8$)-alkyl, ($C_5$–$C_{14}$)-aryl radical, in which 1 to 5 carbon atoms can be replaced by heteroatoms such as N, O, S or ($C_5$–$C_{14}$)-aryl-($C_1$–$C_8$)alkyl, in which 1 to 5 carbon atoms in the aryl part can be replaced by heteroatoms such as N, O, S and $R_{13}$ has the same values as $R_{12}$ with the exception of hydrogen.

Of course, $Ar^1$, $Ar^2$, $Ar^3$, $R^1$, $R^2$, $R^3$, $R^4$, $R^5$, $R^6$, $R^7$, $R^8$, $R^9$, $R^{10}$, $R^{11}$, $R^{12}$ and $R^{13}$ can adopt the definitions above independently of each other.

Among the definitions relating to formula (I), the following preferred values can be mentioned:

$Ar^1$ and $Ar^3$ represent phenyl groups, $Ar^1$ represents a phenyl group and $Ar^3$ represents a heterocycle A is preferably a methylene group, B is preferably a —CH═CH—$CH_2$— or -(cyclopropyl)-$CH_2$-group, the said groups being non substituted or substituted by one or more halogens or ($C_1$–$C_4$)-alkyl, $R^1$ is preferably a hydrogen atom or a methyl or ethyl group non substituted or substituted by fluorine, —OH, —$NH_2$, ($C_1$–$C_8$)-alkyloxy, ($C_1$–$C_8$)-alkylamino, or di-($C_1$–$C_8$)-alkylamino, pyrrolidino or 2-oxo-pyrrolidino.

$R^2$ and $R^3$ are preferably halogen atoms $R^4$ is preferably a hydrogen atom $R^6$ is preferably a hydrogen atom $R^5$ and $R^7$ preferably represent hydrogen $R^8$, $R^9$ and $R^{10}$ preferably represent hydrogen, CN, halogen, —$CF_3$, —$OCF_3$, OH, —$SO_3H$, —P(O) $(OH)_2$, carboxy, —$OSO_3H$, —$OPO_3H$, —$NH_2$, ($C_1$–$C_6$)-alkyl, a non aromatic saturated or unsaturated heterocyclic radical, amino-($C_1$–$C_6$)-alkyl, hydroxy-($C_1$–$C_6$)-alkyl, ($C_1C_6$)-alkyloxy, ($C_1$–$C_6$)-alkylamino-($C_1$–$C_6$)-alkyloxy, ($C_1$–$C_6$)-alkyloxycarbonyl, ($C_1$–$C_6$)-alkylcarbonyl, ($C_1$–$C_6$)-alkylaminocarbonyl, ($C_1$–$C_6$)-alkylamino, di-($C_1$–$C_6$)-alkylamino or di-($C_1$–$C_6$)-alkylamino-($C_1$–$C_6$)-alkyloxy, the said alkyl radicals or heterocycles being non substituted or substituted by halogen, OH, SO₃H, P(O) (OH)₂, oxo, carboxy, —OSO₃H, —OPO₃H₂, —NH₂, phenyl, (C₁–C₆)-alkyl, (C₁–C₆)-alkyloxy, hydroxy-(C₁–C₆)-alkyl, (C₁–C₆)-alkylamino or di-(C₁–C₆)-alkylamino.

A more particular subject of the invention is the compounds of formula (I) as defined above in which A is a CH₂— group, B is a —CH═CH—CH₂— or -Cyclopropyl—CH₂— group, Ar¹ represents a phenyl and Ar² represents a phenylene as well as their physiologically acceptable addition salts.

A more particular subject of the invention is the compound of formula (I) as defined above corresponding to the structure:

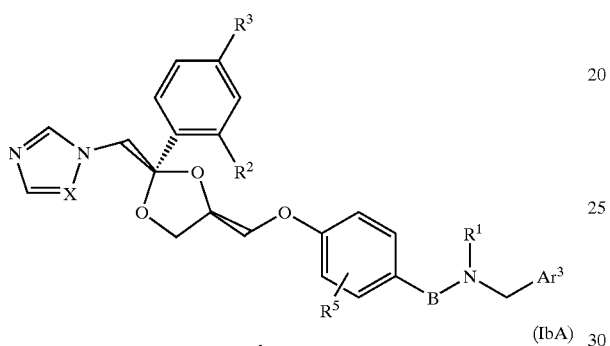

(IaA)

(IbA)

in which, B, X, Ar³, R⁵ and R¹ are as defined above and R² and R³ represent a chlorine or fluorine atom as well as their physiologically acceptable addition salts.

A more particular subject of the invention is the compounds of formula (I) or (IA) (by (IA): (IaA) or (IbA) is meant) as defined above in which R₂ and R₃ are fluorine or chlorine atoms, X represents CH or N and Ar³ represents a phenyl group non substituted or substituted by R⁸ as defined previously, as well as their physiologically acceptable addition salts.

A quite particular subject of the invention is the compounds of formula (I) or (IA) as defined previously, in which R¹ is a hydrogen atom or a methyl or ethyl group non substituted or substituted by an F, OH, NH₂, (C₁–C₆)-alkyloxy, (C₁–C₆)-alkylamino, di-(C₁–C₆)-alkylamino, pyrrolidino or 2-oxo-pyrrolidino group as well as their physiologically acceptable addition salts.

A quite particular subject of the invention is the compounds of formula (IA) as defined previously in which Ar³ is a phenyl non substituted or substituted by R⁸ representing a —Cl, —F, CN, —CF₃, —OCF₃, —OH, —NH₂, (C₁–C₆)-alkyloxy, (C₁–C₆)-alkylamino, di-(C₁–C₆)-alkylamino radical or a heterocycle chosen from:

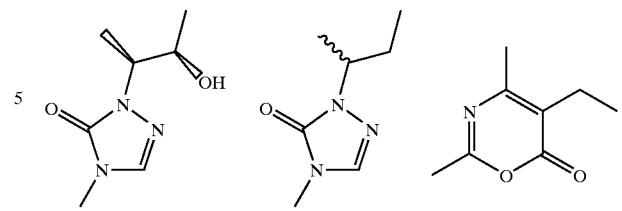

A quite particular subject of the invention is the following compounds:

Alpha-(2,4-dichlorophenyl)-alpha-[[4-[3-[[methyl (phenylmethyl)]amino]]-1(E)-propenyl]phenoxy] methyl]-1H-imidazol-1-ethanol;

Alpha-(2,4-dichlorophenyl)-alpha-[[4-[3-[[methyl(1-naphthalenylmethyl)]amino]-1(E)-propenyl]phenoxy] methyl]-1H-imidazol-1-ethanol.

A subject of the invention is also a process for the preparation of the compounds of formula (Ia) or (Ib) characterized in that a compound of formula (IIa) or (IIb):

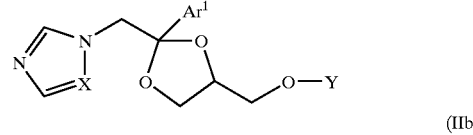

(IIa)

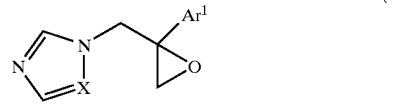

(IIb)

in which —OY represents a leaving group after nucleophilic substitution such as mesylate or tosylate and the other substituents retain their previous meaning is subjected to the action, in the presence of a base, of a compound of formula (III)

HO—Ar²—B—N(R¹)-A-Ar³    (III)

in which Ar², A,R¹,B and Ar³ retain their previous meaning, in order to obtain the corresponding compound of formula (Ia) or (Ib).

This reaction is carried out under standard conditions of nucleophilic substitution of the R—OH+R'—OTs→R—O—R' type known to a person skilled in the art, Ts being a tosyl group. The base used can be in particular sodium hydride and the solvent can be DMF.

The compounds of formula (II) used as starting products are products known in a general fashion, in particular when Ar¹ is a phenyl. They can be prepared according to the process indicated in J. Med. Chem., (1979) 22(8) 1003.

Certain compounds of formula (III) (R¹=Me) are easily accessible. They can be prepared as indicated in the diagram below or in the experimental part.

MEMO—Ph—CH═CH—CHO    +    MeNH—CH₂—Ar³

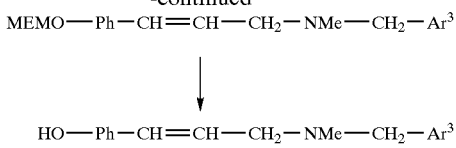

As a variant of the process, the compound of formula (IIa) or (IIb) is reacted with an aryl of formula (III') HO—C$_4$H$_6$—CHO in the presence of a base, the phenyl being non substituted or substituted by R$^5$, in order to obtain a compound of formula (IVa) or (IVb):

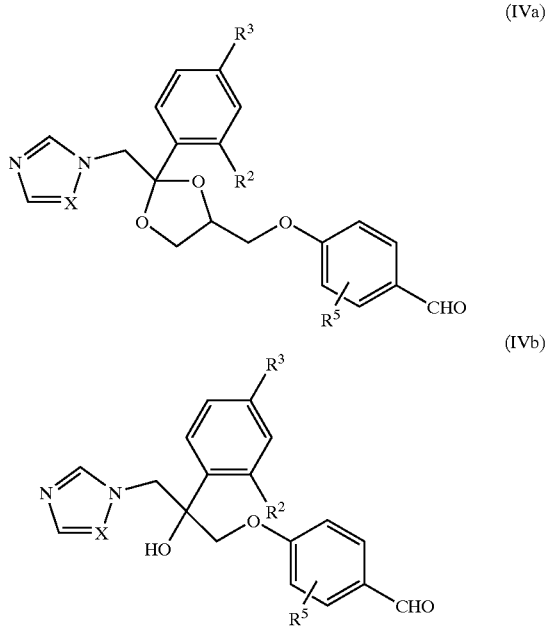

which is successively reacted
- a) with a phosphorane of the (EtO)$_2$POCH$_2$CO$_2$Et type in order to obtain the corresponding unsaturated ester,
- b) with a reducing agent in order to obtain the corresponding alcohol
- c) with an oxidizing agent in order to form the corresponding aldehyde
- d) with an amine of the formula, NHR$^1$-A-Ar$^3$, wherein A, R$^1$ and Ar$^3$ are as defined in claim 1, and then reacting with a reducing agent such as NaBH$_3$CN, in order to obtain the corresponding compounds of formula (Ia) or (Ib).

The starting compounds of formula (IVa) or (IVb) can be prepared according to the processes described in the literature or also are accessible by analogy. The preparation of the compounds of formula (II) is described in Eur. J. Med. Chem., (1995) 30, 617–626 or J. Heterocyclic Chemistry, (1990), 27 2053, it being understood that the present invention not restricted to these syntheses or to these starting products. It is not a major problem for a person skilled in the art to envisage modifications to the syntheses described in our Application for the preparation of other compounds of formula (I) according to the invention.

The compounds of formula (I) are compounds having a pharmacological activity and can thus be used as medicaments in particular as antifungals.

Therefore a subject of the present invention is the compounds of formula (I) and/or their physiologically acceptable salts and/or their prodrugs as a medicament.

The compounds of formula (I) as well as their physiologically acceptable salts and their prodrugs can be administered to animals, preferably to mammals and in particular to human beings as therapeutic or prophylactic medicaments.

The compounds of formula (I) have useful antifungal properties. They are in particular active on *Candida albicans* and other *Candidas* such as *Candida glabrata, krusei, tropicalis, pseudotropicalis* and *parapsilosis,* on *Aspergillus, Aspergillus flavus, Aspergillus niger, Cryptococcus neoformans, Microsporum canis, Trichophyton rubrun, Trichophyton mentagrophyte.*

The compounds of formula (I) can be used as medicaments in man or animals, in particular to combat digestive, urinary, vaginal or cutaneous candidosis, cryptococcosis, for example neuromeningeal, pulmonary or cutaneous cryptococcosis, bronchopulmonary and pulmonary aspergillosis and invasive aspergillosis in the immunosuppressed.

The compounds according to the invention can also be used in the prevention of mycotic illnesses in those with congenital or acquired immunodeficiency.

The compounds of the invention are not limited to a pharmaceutical use, they can also be used as fungicides in fields other than the pharmaceutical field.

A subject of the invention is therefore the compounds of formula (Ia) or (Ib) as antifungal medicaments.

A subject of the invention is also the use of chemical entities having at one end the following groups:

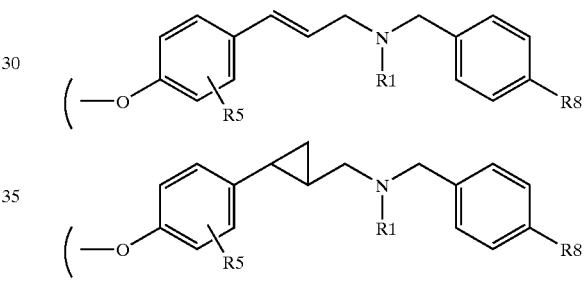

and at the other end a pharmacophore group having a fungicide activity, for example a derivative of azole or triazole as defined previously, for the preparation of medicaments having an antifungal activity.

The compounds according to the invention can be administered neat or in a mixture with one or more other compounds of formula (I) or also in the form of a pharmaceutical preparation (pharmaceutical composition) which allows enteral or parenteral administration and which contains as active compound an effective dose of at least one compound of formula (I) and/or its physiologically acceptable salts and/or its prodrugs as well as standard and pharmaceutically inert supports and/or additives.

The pharmaceutical compositions according to the invention allow enteral or parenteral administration, containing as active compound an effective dose of at least one compound of formula (I) and/or its physiologically acceptable salts and/or its prodrugs as well as one or more pharmaceutically inert supports, and/or one or more usual additives.

A subject of the invention is therefore the pharmaceutical compositions containing a compound of formula (Ia) or (Ib) as defined previously as well as a vehicle.

The medicaments can be administered orally, for example in the form of pills, tablets, coated tablets, flakes, granules, gelatin capsules and soft capsules, solutions, syrups, emulsions, suspensions or aerosol mixtures.

The administration can however be carried out by rectal route, for example in the form of suppositories, by parenteral route, for example in the form of injectable solutions or infusions, microcapsules or implants, by percutaneous route, for example in the form of ointments, solutions, pigments or coloring agents, by transdermal route in the form of patches or by other routes such as in the form of nasal aerosols or sprays.

The pharmaceutical compositions according to the invention are prepared according to methods known per se, pharmaceutically inert organic or inorganic supports being added to the compounds of formula (I) and/or their physiologically acceptable salts and/or their prodrugs. For the production of pills, tablets, coated tablets and hard gelatin capsules, it is possible to use for example, lactose, corn starch or its derivatives, talc, stearic acid or its salts, etc. Suitable supports for soft gelatin capsules or suppositories are for example fats, waxes, semi-solid or liquid polyols, natural or modified oils etc. Appropriate supports for the preparation of solutions, for example injectable solutions, emulsions or syrups are for example water, alcohols, glycerol, polyols, sucrose, inverted sugars, glucose, vegetable oils, etc. Suitable supports for microcapsules or implants are for example glyoxylic acid and lactic acid copolymers. The pharmaceutical preparations normally contain from 0.5% to 90% by weight of compounds of formula (I) and/or their physiologically acceptable salts.

In addition to the active ingredients and supports, the pharmaceutical preparations can contain additives such as for example diluents, disintegrating agents, binders, lubricants, wetting agents, stabilizers, emulsifiers, preservatives, sweeteners, coloring agents, flavoring agents, thickeners, buffering agents, and also solvents or solubilizers or agents for obtaining a delayed effect and also salts for modifying the osmotic pressure, coating agents or antioxidants.

They can also contain two or more compounds of formula (I) and/or their physiologically acceptable salts and/or their prodrugs. Moreover, in more than at least one or more compounds of formula (I) and/or their physiologically acceptable salts and/or their prodrugs, they can contain at least one or more other useful active ingredients as therapeutics or prophylactics.

The pharmaceutical preparations (pharmaceutical compositions) normally contain from 0.2 to 500 mg, and preferably from 1 to 200 mg of the compound of formula (I) and/or their physiologically acceptable salts and/or their prodrugs.

A more particular subject of the present invention is therefore a compound of formula (I) and/or its physiologically acceptable salts and/or its prodrugs as defined above as a medicament having an antifungal activity.

A subject of the present invention is also the use of the compounds of formula (I) and/or their physiologically acceptable salts and/or their prodrugs as defined above for the preparation of antifungal medicaments.

When the compounds of formula (I) are used, the doses can vary within broad limits and must be fixed as a function of the person to be treated. This depends for example on the compound used or the nature and severity of the disease to be treated and whether serious or chronic conditions prevail or a prophylactic treatment is being implemented.

In the case of administration by oral route, the daily dose generally varies from 0.01 to 100 mg/kg and preferably from 0.1 to 50 mg/kg, in particular from 0.1 to 5 mg/kg.

In the case of administration by intravenous route, the daily dose varies approximately from 0.01 to 100 mg/kg and preferably from 0.05 to 10 mg/kg. The daily dose can be divided, in particular in the case of the administration of a large quantity of active ingredient, into several, for example 2, 3 or 4 parts. If appropriate, as a function of individual behavior, it can be necessary to administer the different doses in increasing or decreasing manner.

The compounds of formula (I) and their salts can also be used as intermediates for the preparation of other compounds, in particular other active ingredients, which are accessible from the compounds of formula (I), for example by modification or introduction of radicals or functional groups.

EXAMPLES

The products were identified by mass spectrum (MS), infrared (IR) and/or NMR spectrum. The compounds were purified by normal-phase (in particular in the presence of a $CH_2C_{12}$/MeOH mixture) or reversed-phase chromatography (in the presence of acetic or trifluoroacetic acid). The compounds of formula (I) purified using an eluent which contains for example trifluoroacetic acid, and which are then dried or in which, during the last synthesis stage, for example trifluoroacetic acid was used in order to eliminate a tert-butyl protective group, sometimes contain, depending on the manner in which the product was dried, the acid originating from the eluent or the last synthesis stage and are therefore found partially or completely in the form of the salt of the acid used, for example in the form of an acetic or trifluoroacetic acid salt. They can also be more or less hydrated.

Abbreviations/Chemical Names Optionally Used:

AcOEt: ethyl acetate; DMF: dimethylformamide; HOBt: 1-hydroxybenzotriazole hydrate, MeOH: methanol; TEA: triethylamine; TFA: trifluoroacetic acid; THF: tetrahydrofuran; MCPBA: meta-chloroperoxybenzoic acid; DBU: 1,8-diazabicyclo[5.4.0]undec-7-ene; PTSA: paratoluenesulfonic acid; DPPA: diphenylphosphorylazide; DMSO: dimethylsulfoxide; Pd/C Palladium on carbon; Boc: tert-butoxycarbonyl; CBz: benzyloxycarbonyl; DCC 1,3-dicyclohexylcarbodiimide; IR: Infrared; NMR: Nuclear Magnetic Resonance; MS: Mass Spectrum; PES: Positive mode electrospray; sh.: shoulder; S: strong; s: singlet; d: doublet; t: triplet; quad: quadruplet; quint: quintuplet; b: broad; m: multiplet; J: coupling constant; Rf: retention factor (chromatography). The NMR spectra below were interpreted and the aromatic hydrogens are identified thus

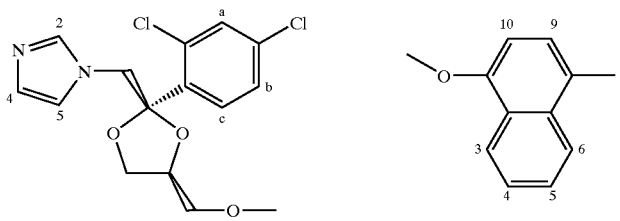

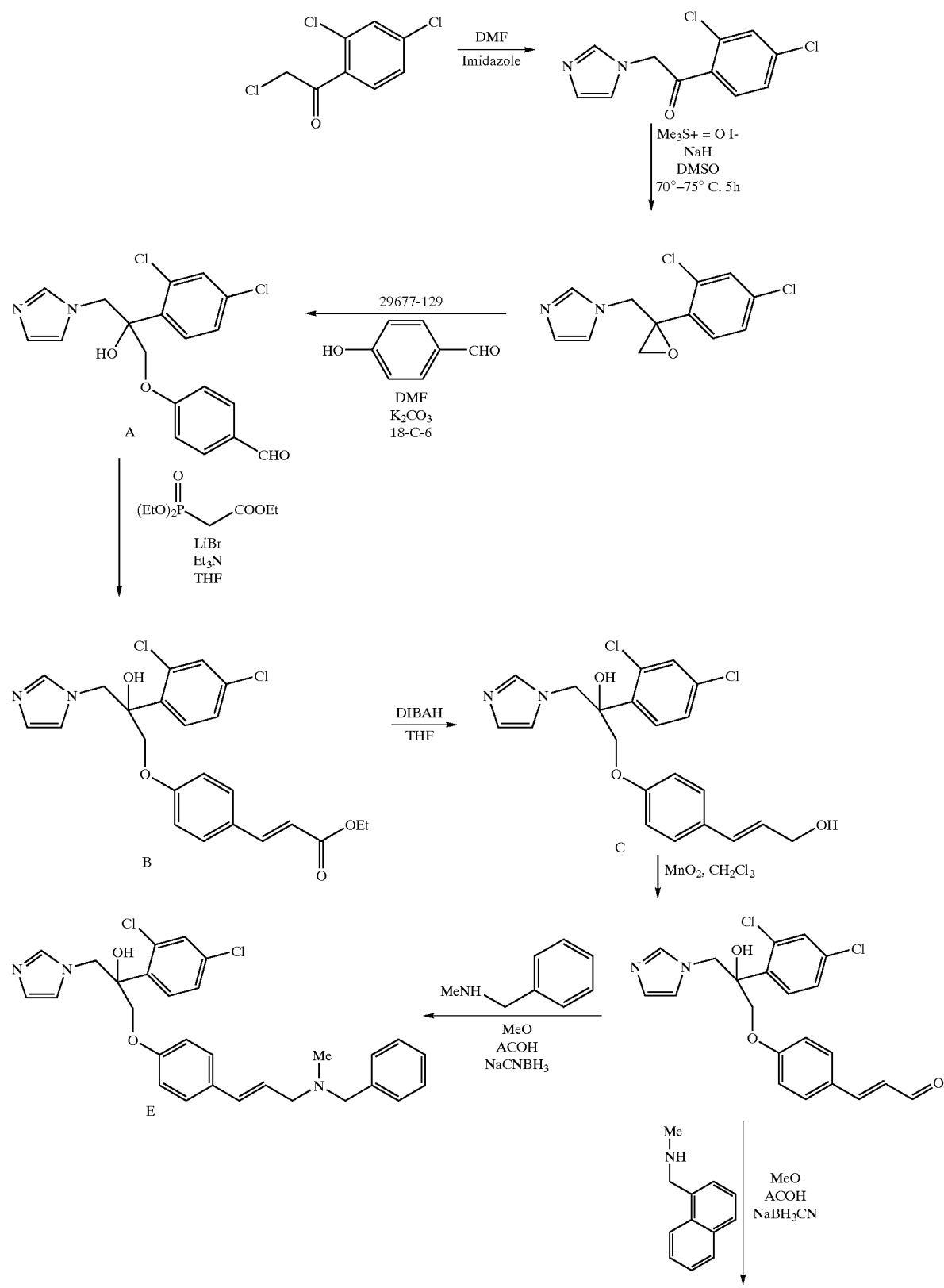

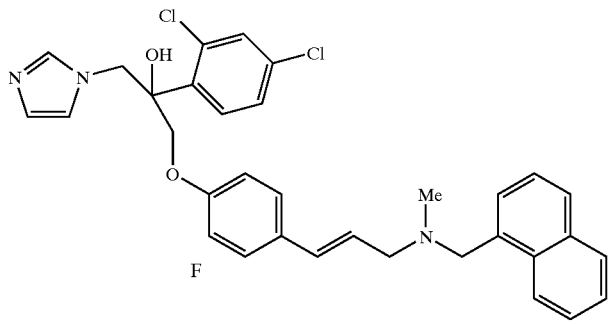

Example 1

Alpha-(2,4-dichlorophenyl)-alpha-[[4-[3-[[methyl(phenylmethyl)]amino]]-1(E)-propenyl]phenoxy]methyl]-1H-imidazol-1-ethanol

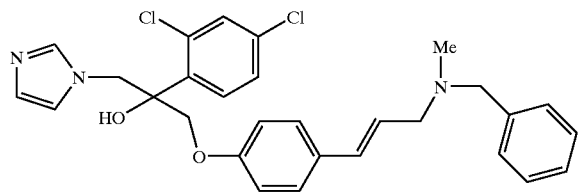

Stage a: A→B

Lithium bromide (1.38 g) is introduced into a solution of triethylphosphonoacetate (3.16 ml) in THF (13 ml), followed by agitating for 10 minutes at ambient temperature. Then triethylamine (2.24 ml) is added and agitation is continued for 10 minutes at ambient temperature. Then a suspension of aldehyde IVb (X=CH, $R_2=R_3$=Cl, 1.56 g) in 15 ml of THF is added rapidly, followed by agitating for 24 hours at 25° C., heating at 55° C. for 4 hours, cooling down, extracting with dichloromethane then washing with water. The organic phase is dried ($MgSO_4$), followed by filtering and evaporating in order to obtain 3.6 g of crude product which is purified by chromatography on silica eluting with a dichloromethane/methanol mixture (96/4). The expected product is obtained.

TLC (silica, $CH_2Cl_2$—MeOH, 96:4) Rf=0.25.

Stage b: B→C

A solution of the product of Stage a (1.19 g, 2.6 mmol) in THF (11 ml) is cooled down to 0° C. then a solution of DIBAH (3.4 ml, 1.5 M) in toluene is added while maintaining the temperature below 10° C. After agitating for 2 hours, the reaction medium is left to return to 15° C. and a solution of DIBAH (8.5 ml, 1.5 M) in toluene is added while maintaining the temperature at 15° C. After agitating at ambient temperature for 48 hours, the solution is then cooled down to 0° C. and 5 ml of a saturated solution of sodium and potassium double tartrate is poured in, followed by agitating for 1 hour at ambient temperature. After having diluted with 15 ml of water, extraction is carried out with 3×50 ml of $CH_2Cl_2$, followed by drying over $MgSO_4$, filtering and evaporating to dryness in order to obtain the crude product (0.83 g), which is purified by chromatography on silica eluting with a dichloromethane/methanol mixture (96/4) in order to obtain the expected product.

TLC (silica, $CH_2Cl_2$—MeOH, 96:4) Rf=0.15.

Stage c: C→D $MnO_2$ (1.07 g) is introduced in one step into a solution of the product of Stage b (0.52 g) in dichloromethane (12 ml), and agitation is carried out for 48 hours at ambient temperature, followed by filtering on Clarcel flow M, washing with $CH_2Cl_2$ and evaporating to dryness in order to produce the sought product (0.46 g).

TLC (silica, $CH_2Cl_2$—MeOH, 96:4) Rf=0.3.

Stage d: D→E

N-methylbenzylamine (0.04 g) and acetic acid (23 µl) are added, at ambient temperature, to a solution of the product of Stage c (0.125 g) in methanol (1.2 ml). Agitation is carried out for 10 minutes before adding $NaBH_3CN$ (20 mg). After agitating for 4 hours, water and dichloromethane are added, followed by adjusting to pH 8 with a solution of concentrated ammonium hydroxide, extracting with dichloromethane, drying over $MgSO_4$, filtering and evaporating to dryness under vacuum in order to produce the crude product (0.17 g).

Purification is carried out by chromatography on silica eluting with a dichloromethane/methanol mixture (96/4) in order to obtain the expected product (38 mg, RU 831624).

TLC (silica, $CH_2Cl_2$—MeOH—NH4OH, 96:4:0.1) Rf=0.15.

Example 2

Alpha-(2,4-dichlorophenyl)-alpha-[[4-[3-[[methyl(1-naphthalenylmethyl)]amino]-1(E)-propenyl]phenoxy]methyl]-1H-imidazol-1-ethanol

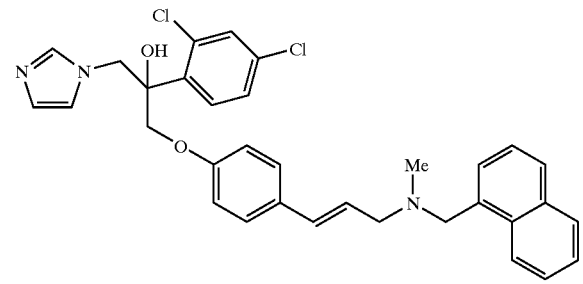

Stage d': D→F

The above product is prepared in a similar manner to Example 1.

TLC (silica, $CH_2Cl_2$—MeOH, 95:5) Rf=0.3.

Pharmaceutical Compositions

Compounds were prepared containing

| Product of Example 1 | 50 mg |
|---|---|
| Excipient q.s.f. | 1 g |

Detail of the excipient: starch, talc, and magnesium stearate.

Biological Activity

1) Antifungal Activity of the Compounds According to the Invention.

Female mice weighing from 18 to 22 g were used. A quantity of *Candida albicans* 44858 was administered into the tail vein at a rate of $10^6$ CFU per mouse (CFU: colony forming unit). The mice are separated into 5 groups of 5 mice and treated as follows:

One hour after the infection

Group 1: the mice are treated with the product P 25 mg/kg by oral route

Group 2: the mice are treated with the product P by intraperitoneal route at a rate of 25 mg/kg Group 3: the mice are treated with fluconazole (25 mg/kg by oral route).

Group 4: the mice are treated with fluconazole (25 mg/kg by intraperitoneal route).

Group 5: the mice receive no antifungal treatment.

Over a period of 22 days, the dead mice are counted.

2) Minimum Inhibiting Concentration (MIC)

*Candida albicans* cells are prepared as indicated in Journal of Antimicrobial Chemotherapy 38, 579–587, washed 3 times with a 0.1 M phosphate solution and used immediately in order to determine the minimum inhibiting concentration (MIC).

The MICs are determined by the modification of a microtitration plate according to the standard method of the Comité National des standards cliniques de laboratoire. RPMI-1640 is used as medium, and L-glutamine buffered to pH 7 with a 0.15 M MOPS (3-[N-morpholino]propane sulfonic acid) solution. *Candida albicans* cells ($1.5 \times 10^3$ cells/ml) are added to the wells of a 96-well plate containing RPMI-1640 and the antifungal agent dilutions. The results were read 48 hours after incubation at 35° C. and the MIC or minimum inhibiting concentration which inhibits the growth of *Candida albicans* cells was determined.

Minimum Fungicidal Concentration

After the MIC reading at 48 hours, the plates are shaken and 10 μL of aliquot is removed from the wells, and placed on rectangular disks containing dextrose agar. The plates are incubated for 48 hours at 35° C. The minimum fungicidal concentration is the concentration of the antifungal agent at which the number of colony forming units is zero.

Conclusion

The compounds according to the invention described in Examples 1 to 2 show an activity <100 μg/ml in the MIC test.

What is claimed is:

1. A compound of formula (Ia) or (Ib):

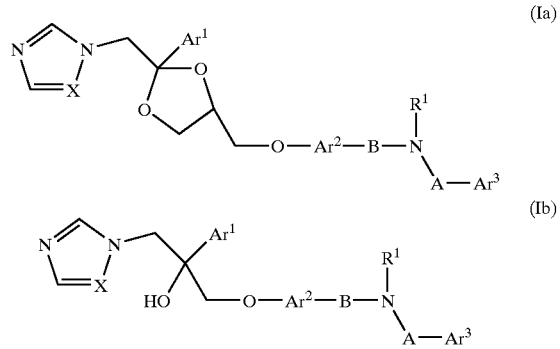

wherein

X is N or CH;

$Ar^1$ is a carbocyclic or heterocyclic aryl non substituted or substituted by one or more $R^2$, $R^3$ or $R^4$;

$Ar^2$ is phenylene or naphthalene non substituted or substituted by one or more $R^5$, $R^6$ or $R^7$;

$Ar^3$ is a carbocyclic or heterocyclic aryl non substituted or substituted by one or more $R^8$, $R^9$ or $R^{10}$;

A is $(C_1-C_4)$-alkylene;

B is —CH=CH—$(C_1-C_4)$-alkylene- or -cyclopropylene-$(C_1-C_4)$-alkylene-, wherein said cyclopropylene or —CH=CH— being non substituted or substituted by $R^2$ or $R^3$;

$R^1$ is hydrogen, —$SO_3H$ or $(C_1-C_6)$-alkyl non substituted or substituted by $R^2$ or alkylene linked to $Ar^3$;

$R^2$, $R^3$, $R^4$, $R^5$, $R^6$, $R^7$, $R^8$, $R^9$ or $R^{10}$, identical or different, are independently selected from the group consisting of: fluorine, chlorine, bromine, cyano, mono-bi- or trihalogeno$(C_1-C_8)$alkyl, mono-bi- or trihalogeno$(C_1-C_8)$-alkyloxy, hydroxy, nitro, carboxyl, formyl, —$SO_3H$, —$OSO_3H$, $(R^{11}O)_2P(O)$—, $(R^{11}O)_2P(O)$—O—, amino, $(C_1-C_8)$-alkylamino, di$((C_1-C_8)$alkyl)amino, $(C_5-C_{14})$-aryl-$(C_1-C_6)$-alkylenamino or $(C_5-C_{14})$-arylamino, $(C_1-C_8)$-alkyl, $(C_5-C_{14})$-aryl, a heterocycle optionally substituted by oxo, $(C_5-C_{14})$-aryl-$(C_1-C_6)$alkyl, amino-$(C_1-C_6)$-alkyl, $(C_1-C_8)$-alkylamino-$(C_1-C_6)$-alkyl, di-$((C_1-C_8)$alkyl)amino-$(C_1-C_6)$-alkyl, hydroxy-$(C_1-C_6)$alkyl, $(C_1-C_6)$-alkyloxy-$(C_1-C_6)$-alkyl, $(C_1-C_8)$-alkyloxy optionally interrupted by one or more oxygen atoms, $(C_5-C_{14})$-aryl-$(C_1-C_6)$-alkylenoxy, $(C_5-C_{14})$-aryloxy, hydroxy-$(C_1-C_6)$ alkylenoxy, $(C_1-C_6)$-alkyloxy-$(C_1-C_6)$ alkylenoxy, amino-$(C_1-C_6)$-alkylenoxy, $(C_1-C_6)$-alkylamino-$(C_1-C_6)$-alkylenoxy, di$((C_1-C_8)$-alkyl)amino-$(C_1-C_6)$-alkylenoxy, methylenedioxy, $(C_1-C_6)$-alkyloxycarbonyl, $(C_1-C_6)$-alkylcarbonyl, $(C_5-C_{14})$ aryl-$(C_1-C_6)$-alkylenecarbonyl, $(C_5-C_{14})$-arylcarbonyl, $(C_1-C_6)$-alkylaminocarbonyl, $(C_1-C_6)$ alkanoylamino, $(C_1-C_6)$-alkylsulfonylamino, $(C_5-C_{14})$-arylsulfonylamino, $(C_5-C_{14})$-aryl-$(C_1-C_6)$-alkylenesulfonylamino, $(C_1-C_6)$-alkylaminosulfonyl, $(C_5-C_{14})$-aryl-$(C_1-C_6)$-alkylenaminosulfonyl, $(C_1-C_6)$-alkylsulfonyl, $(C_5-C_{14})$-aryl-$(C_1-C_8)$-alkylenesulfonyl or $(C_5-C_{14})$-aryl-sulfonyl, wherein said alkyl, aryl or heterocycle being themselves non substituted or substituted by one or more of the groups mentioned above;

$R^{11}$ is hydrogen, $(C_1-C_{10})$-alkyl, $(C_6-C_{14})$-aryl or $(C_6-C_{14})$-aryl-$(C_1-C_6)$-alkyl;

or a stereoisomeric form or a mixture thereof, or a physiologically acceptable addition salt thereof or a prodrug thereof.

2. The compound of formulae (Ia) or (Ib) as set forth in claim 1, wherein A is —CH$_2$—, B is —CH=CH—CH$_2$— or -cyclopropyl-CH$_2$— and Ar$^1$ is phenyl and Ar$^2$ is phenylene or a physiologically acceptable addition salt thereof.

3. The compound as set forth in claim 1 having the following formulae (IaA) or (IbA):

(IaA)

(IbA)

wherein, B, X, Ar$^3$, R$^5$ and R$^1$ are as defined in claim 1 and R$^2$ and R$^3$ are halogen or a physiologically acceptable addition salt thereof.

4. The compound of formulae (Ia) or (Ib) as set forth in claim 1 wherein R$_2$ and R$_3$ are chlorine, X is CH or N and Ar$^3$ is phenyl non substituted or substituted by R$^8$ wherein R$^8$ is as defined in claim 1 or a physiologically acceptable addition salt thereof.

5. The compound of formulae (IaA) or (IbA) as set forth in claim 3 wherein R$_2$ and R$_3$ are chlorine, X is CH or N and Ar$^3$ is phenyl non substituted or substituted by R$^8$ wherein R$^8$ is as defined in claim 1 or a physiologically acceptable addition salt thereof.

6. The compound of formulae (Ia) or (Ib) as set forth in claim 1 wherein, R$^1$ is hydrogen or methyl or ethyl non substituted or substituted by F, OH, NH$_2$, (C$_1$–C$_6$)-alkyloxy, (C$_1$–C$_6$)-alkylamino, di-(C$_1$–C$_6$)-alkylamino, pyrrolidino or 2-oxo-pyrrolidino, or a physiologically acceptable addition salt thereof.

7. The compound of formulae (IaA) or (IbA) as set forth in claim 3 wherein, R$^1$ is hydrogen or methyl or ethyl non substituted or substituted by F, OH, NH$_2$, (C$_1$–C$_6$)-alkyloxy, (C$_1$–C$_6$)-alkylamino, di-(C$_1$–C$_6$)-alkylamino, pyrrolidino or 2-oxo-pyrrolidino, or a physiologically acceptable addition salt thereof.

8. The compound of formulae (Ia) or (Ib) as set forth in claim 1 wherein Ar$^3$ is phenyl non substituted or substituted by R$^8$ and wherein R$^8$ is —Cl, —F, CN, —CF$_3$, —OCF$_3$, —OH, —NH$_2$, (C$_1$–C$_6$)-alkyloxy, (C$_1$–C$_6$)-alkylamino, or di-(C$_1$–C$_6$)-alkylamino or heterocycle chosen from:

or a physiologically acceptable addition salt thereof.

9. The compound of formulae (IaA) or (IbA) as set forth in claim 3 wherein Ar$^3$ is phenyl non substituted or substituted by R$^8$ and wherein R$^8$ is —Cl, —F, CN, —CF$_3$, —OCF$_3$, —OH, —NH$_2$, (C$_1$–C$_6$)-alkyloxy, (C$_1$–C$_6$)-alkylamino, or di-(C$_1$–C$_6$)-alkylamino or heterocycle chosen from:

or a physiologically acceptable addition salt thereof.

10. The compound of formula (Ib) as set forth in claim 1 which is selected from the group consisting of:

alpha-(2,4-dichlorophenyl)-alpha-[[4-[3-[[methyl(phenylmethyl)]amino]]-1(E)-propenyl]phenoxy]methyl]-1H-imidazol-1-ethanol; and alpha-(2,4-dichlorophenyl)-alpha-[[4-[3-[[methyl(1-naphthalenylmethyl)]amino]-1(E)-propenyl]phenoxy]methyl]-1H-imidazol-1-ethanol.

11. A process for the preparation of a compound of formula (Ia) or (Ib) according to claim 1 comprising:

reacting a compound of formulae (IIa) or (IIb)

(IIa)

(IIb)

wherein —OY is a leaving group such as mesylate or tosylate, X and Ar$^1$ are as defined in claim 1, in the presence of a base, with a compound of formula (III):

HO—Ar$^2$—B—N(R$^1$)-A-Ar$^3$    (III)

wherein Ar$^2$, Ar$^3$, A, B and R$^1$ are as defined in claim 1, in order to obtain the corresponding compound of formula (I).

12. A process for the preparation of a compound of formula (I) according to claim 1 comprising:

(a) reacting a compound of formulae (IIa') or (IIb')

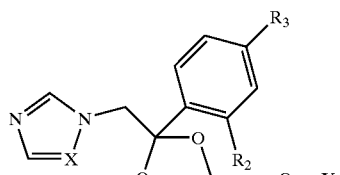
(IIa')

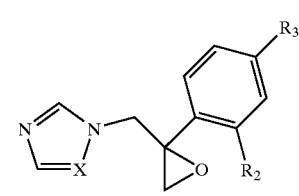
(IIb')

wherein —OY is a leaving group such as mesylate or tosylate, X, $R^2$ and $R^3$ are as defined in claim 1, with an aryl of formula (III'), HO—$C_6H_4$—CHO, in the presence of a base, the phenylene being non-substituted or substituted by $R^5$, wherein $R^5$ is as defined in claim 1, in order to obtain a compound of formulae (IVa) or (IVb):

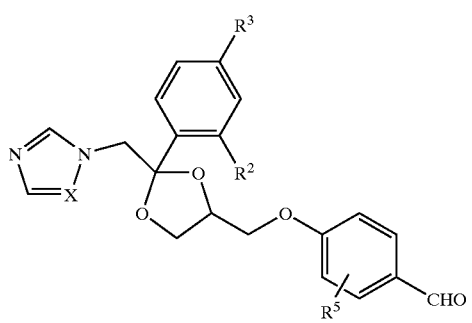
(IVa)

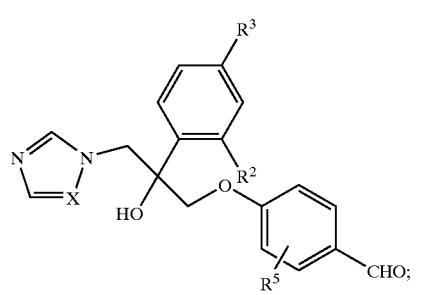
(IVb)

(b) reacting compound of formula (IVa) or (IVb) successively:
(c) with a phosphorane of formula, $(EtO)_2POCH_2CO_2Et$, in order to obtain the corresponding allylic ester;
(d) with a reducing agent in order to obtain the corresponding alcohol;
(e) with an oxidizing agent in order to form the corresponding aldehyde; and
(f) with an amine of the formula, $NHR^1$-A-$Ar^3$, wherein A, $R^1$ and $Ar^3$ are as defined in claim 1, and then reacting with a reducing agent such as $NaBH_3CN$, in order to obtain the corresponding compound of formulae (Ia) or (Ib).

13. A pharmaceutical composition comprising at least one compound of formula (Ia) or (Ib) and a pharmaceutically acceptable vehicle:

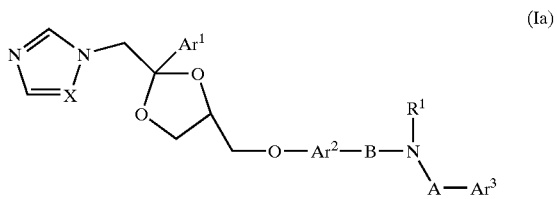
(Ia)

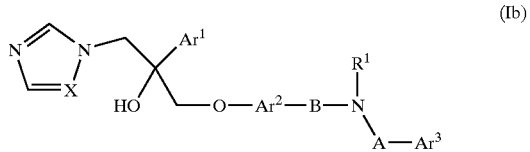
(Ib)

wherein

X is N or CH;

$Ar^1$ is a carbocyclic or heterocyclic aryl non substituted or substituted by one or more $R^2$, $R^3$ or $R^4$;

$Ar^2$ is phenylene or naphthalene non substituted or substituted by one or more $R^5$, $R^5$ or $R^7$;

$Ar^3$ is a carbocyclic or heterocyclic aryl non substituted or substituted by one or more $R^8$, $R^9$ or $R^{10}$;

A is $(C_1-C_4)$-alkylene;

B is —CH=CH—$(C_1-C_4)$-alkylene- or -cyclopropylene-$(C_1-C_4)$-alkylene-, wherein said cyclopropylene or —CH=CH— being non substituted or substituted by $R^2$ or $R^3$;

$R^1$ is hydrogen, —$SO_3H$ or $(C_1-C_6)$-alkyl non substituted or substituted by $R^2$ or alkylene linked to $Ar^3$;

$R^2$, $R^3$, $R^4$, $R^5$, $R^6$, $R^7$, $R^8$, $R^9$ or $R^{10}$, identical or different, are independently selected from the group consisting of: fluorine, chlorine, bromine, cyano, mono-bi- or trihalogeno$(C_1-C_8)$alkyl, mono-bi- or trihalogeno$(C_1-C_8)$-alkyloxy, hydroxy, nitro, carboxyl, formyl, —$SO_3H$, —$OSO_3H$, $(R^{11}O)_2P(O)$—, $(R^{11}O)_2P(O)$—O—, amino, $(C_1-C_8)$-alkylamino, di$((C_1-C_8)$ alkyl)amino, $(C_5-C_{14})$-aryl-$(C_1-C_6)$-alkylenamino or $(C_5-C_{14})$-arylamino, $(C_1-C_8)$-alkyl, $(C_5-C_{14})$-aryl, a heterocycle optionally substituted by oxo, $(C_5-C_{14})$-aryl-$(C_1-C_6)$alkyl, amino-$(C_1-C_6)$-alkyl, $(C_1-C_8)$-alkylamino-$(C_1-C_6)$-alkyl, di-$((C_1-C_8)$alkyl)amino-$(C_1-C_6)$-alkyl, hydroxy-$(C_1-C_6)$alkyl, $(C_1-C_6)$-alkyloxy-$(C_1-C_6)$-alkyl, $(C_1-C_8)$-alkyloxy optionally interrupted by one or more oxygen atoms, $(C_5-C_{14})$-aryl-$(C_1-C_6)$-alkylenoxy, $(C_5-C_{14})$-aryloxy, hydroxy-$(C_1-C_6)$alkylenoxy, $(C_1-C_6)$-alkyloxy-$(C_1-C_6)$ alkylenoxy, amino-$(C_1-C_6)$-alkylenoxy, $(C_1-C_6)$-alkylamino-$(C_1-C_6)$-alkylenoxy, di$((C_1-C_8)$-alkyl)amino-$(C_1-C_6)$-alkylenoxy, methylenedioxy, $(C_1-C_6)$-alkyloxycarbonyl, $(C_1-C_6)$-alkylcarbonyl, $(C_5-C_{14})$ aryl-$(C_1-C_6)$-alkylenecarbonyl, $(C_5-C_{14})$-arylcarbonyl, $(C_1-C_6)$-alkylaminocarbonyl, $(C_1-C_6)$ alkanoylamino, $(C_1-C_6)$-alkylsulfonylamino, $(C_5-C_{14})$-arylsulfonylamino, $(C_5-C_{14})$-aryl-$(C_1-C_6)$-alkylenesulfonylamino, $(C_1-C_6)$-alkylaminosulfonyl, $(C_5-C_{14})$-aryl-$(C_1-C_6)$-alkylenaminosulfonyl, $(C_1-C_6)$-alkylsulfonyl, $(C_5-C_{14})$-aryl-$(C_1-C_8)$- alkylenesulfonyl or (C$_5$–C$_{14}$)-aryl-sulfonyl, wherein said alkyl, aryl or heterocycle being themselves non substituted or substituted by one or more of the groups mentioned above;

R$^{11}$ is hydrogen, (C$_1$–C$_{10}$)-alkyl, (C$_6$–C$_{14}$)-aryl or (C$_6$–C$_{14}$)-aryl-(C$_1$–C$_6$)-alkyl;

or a stereoisomeric form or a mixture thereof, or a physiologically acceptable addition salt thereof or a prodrug thereof.

14. The composition as set forth in claim 13 wherein said compound is selected from the group consisting of:
- alpha-(2,4-dichlorophenyl)-alpha-[[4-[3-[[methyl(phenylmethyl)]amino]]-1(E)-propenyl]phenoxy]methyl]-1H-imidazol-1-ethanol; and
- alpha-(2,4-dichlorophenyl)-alpha-[[4-[3-[[methyl(1-naphtalenylmethyl)]amino]-1(E)-propenyl]phenoxy]methyl]-1H-imidazol-1-ethanol.

* * * * *